United States Patent [19]

Sandine et al.

[11] Patent Number: 5,759,843
[45] Date of Patent: Jun. 2, 1998

[54] BACTERIAL COMPOSITIONS FOR INHIBITING FOOD SPOILAGE

[75] Inventors: William E. Sandine, Corvallis, Oreg.; Nageb S. Al-Zoreky, Sana'a, Yemen

[73] Assignee: State of Oregon, by and through the Oregon State Board of Higher Education on behalf of Oregon State University, Corvallis, Oreg.

[21] Appl. No.: 601,350

[22] Filed: Feb. 16, 1996

Related U.S. Application Data

[60] Continuation-in-part of Ser. No. 317,181, Oct. 3, 1992, abandoned, which is a division of Ser. No. 951,809, Sep. 28, 1992, abandoned.

[51] Int. Cl.$^6$ ........................................... C12N 1/20
[52] U.S. Cl. ........................................ 435/252.9; 424/93.45
[58] Field of Search ........................ 435/252.9; 424/93.45

[56] References Cited

U.S. PATENT DOCUMENTS

| | | |
|---|---|---|
| 4,599,313 | 7/1986 | Gonzalez . |
| 4,874,704 | 10/1989 | Boudreaux et al. . |
| 4,912,047 | 3/1990 | Matrozza . |
| 5,186,962 | 2/1993 | Hutkins et al. . |

OTHER PUBLICATIONS

White, et al., J. Food Protection 42, 51–54 (1979).
Griffiths, et al., J. Soc. Dairy Tech. 44, 24–29 (1991).
Marshall, et al., Can. J. Microbiol. 37, 594–599 (1991).
Difco Manual, pp. 546–550, 10th Edition.
Difco Manual, pp. 324–326, 10th Edition.
Roberts and Torrey (J. Dairy Sci. 71:52–60) (1988).
Muriana, P. M., et al., Applied and Env. Microbiology. pp. 553–560 (1987).
Gilliland, S.E., et al., J. Dairy Sci. 66:974–980 (1983).
Champagne, C. P., Biotechnology Letters vol. 12, No. 10 771–776 (1990).
Fontaine, E.A., et al., J. of Applied Bacteriology. 69, 326–331 (1990).
Potter, N. N., Food Science, third edition, 378–379, AV1 Publishing Co., Inc. (Westport) (1978).

*Primary Examiner*—Irene Marx
*Attorney, Agent, or Firm*—Ian C. McLeod

[57] ABSTRACT

A novel strain, Lactobacillus sp. AS-1A (ATCC No. 69890) is described for use in inhibiting bacteria in foods, particularly at refrigeration temperatures. Lactobacillus sp. AS-1A (ATCC No. 69890) is particularly effective in inhibiting bacteria present in raw milk and pasteurized milk.

4 Claims, 3 Drawing Sheets

BACTERIAL COMPOSITIONS FOR INHIBITING FOOD SPOILAGE

CROSS REFERENCE TO RELATED APPLICATION

This application is a continuation-in-part of application Ser. No. 08/317,181, filed Oct. 3, 1994, which in turn is a divisional of application Ser. No. 07/951,809, filed Sep. 28, 1992 all now abandoned.

BACKGROUND OF THE INVENTION

(1) Field of the Invention

The present invention relates to a method and bacterial compositions which use cells of Lactobacillus sp. AS-1A (ATCC No. 69890) to inhibit spoilage in foods. In particular, the present invention relates to a lactic acid producing bacterium which can be used to prevent spoilage in foods at refrigeration temperatures and which does not produce significant amounts of lactic acid in the food.

(2) Prior Art

Lactic acid bacteria have been used to inhibit pathogens and spoilage bacteria in milk and other foods as evidenced by U.S. Pat. Nos. 4,599,313 to Gonzalez and 4,912,047 to Matrozza and by White et al., J. Food Protection 42, 51–54 (1979) and Griffiths et al, J. Soc. Dairy Tech. 44, 24–29 (1991). A paper was presented in a meeting of the Institute of Food Technologists in June, 1991 describing the use of lactic acid bacteria in milk to inhibit pathogens and spoilage. The specific strain used was not identified or described. The bacterial compositions described are effective; however, there is a need for a more effective bacterial composition, particularly one for use in raw milk. One particular problem is that most lactic acid bacteria of the prior art produce sufficient lactic acid even at low temperatures so as to render raw milk unsuitable for pasteurization. Heating raw milk in pasteurizer units when the milk pH is 5.0 or below causes deposit of denatured milk proteins on heating surfaces.

In some countries several days may elapse before raw milk is pasteurized. During that time pathogens and spoilage bacteria can grow and render the milk unfit for its intended use. The legal bacterial count of raw milk is $1 \times 10^5 - 3 \times 10^5$ (100,000 for individual producers—300,000 for co-mingled milk) colony-forming units (CFU)/ml. Psychrotrophic bacteria grow at low temperatures (4°–5° C. or 40°–41° F.) and degrade proteins and fat of raw milk and enzymes from these bacteria survive even ultra high temperature (UHT) pasteurization.

Temperature abuse occurs and spoilage and pathogenic bacteria grow reducing quality and safety of the raw milk. Raw milk is stored at 40° F. before pasteurization for transportation to dairy plants. There may be a short supply of raw milk to large dairy plants and thus there is a need for a reliable and effective method for preserving the raw milk.

The problems with raw milk are present with other refrigerated foods where temperature abuse can occur. Fluid or semi-fluid dairy products, such as yogurt, sour cream, cream and Cottage cheese particularly have problems.

OBJECTS

It is therefore an object of the present invention to provide a Lactobacillus sp. which is uniquely suited to inhibiting spoilage in foods. It is particularly an object of the present invention to provide a Lactobacillus sp. which inhibits spoilage in raw milk and other refrigerated fluid dairy products. These and other objects will become increasingly apparent by reference to the following description and the drawings.

IN THE DRAWINGS

GENERAL DESCRIPTION

Figure 1A:
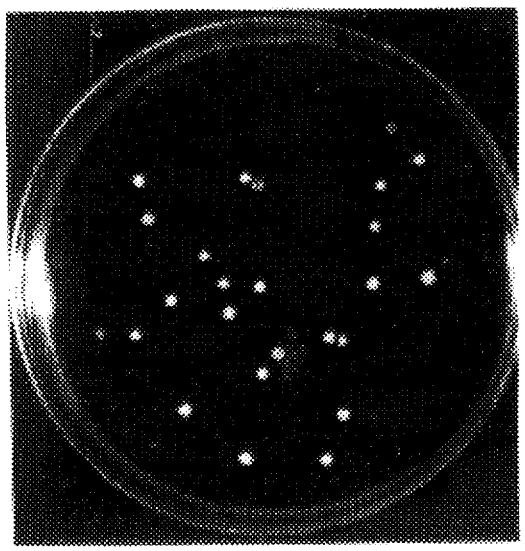
FIG. 1 is a photograph showing the quantity of gram negative bacteria present when raw milk inoculated with $10^2$ Pseudomonas aeruginosa per ml and incubated at 2°–5° C. for 7 days in the presence (left) or absence (right) of inhibitory Lactobacillus sp. AS-1 (ATCC No. 55326) after spread plating on CVT agar and incubating at 32° C. for 48 hours.

The present invention relates to a method for inhibiting bacteria in a refrigerated food by introducing a bacterium into the food, the improvement which comprises providing an effective amount of Lactobacillus sp. AS-1A (ATCC No. 69890) in the refrigerated food to thereby inhibit the psychrotrophic bacteria.

Further the present invention relates to a method of inhibiting bacteria in refrigerated raw milk by introducing a Lactobacillus into the raw milk, the improvement which comprises providing cells of Lactobacillus sp. AS-1A (ATCC No. 69890) in the raw milk, wherein the Lactobacillus sp. inhibits bacteria in the raw milk.

Finally the present invention relates to a bacterial composition which comprises cells of Lactobacillus sp. AS-1A (ATCC No. 69890) free of other cells.

The term "spoilage" means the growth of pathogens in the food or the growth of psychrotrophic bacteria in the food. In either case the food is spoiled.

The foods which can be preserved are raw milk, pasteurized milk or cream of various milk or vegetable fat contents, Cottage cheese, cream cheese, Mexican style white cheese, cultured buttermilk, cultured sour cream, butter and the like. In particular, refrigerated dairy products, such as raw milk, Cottage cheese, sour cream, cream yogurt and the like can be preserved by the methods and compositions of the present invention.

Lactobacillus sp. AS-1 (ATCC No. 55326) was deposited on May 27, 1992 under the Budapest Treaty with the American Type Culture Collection in Rockville, Md. Lactobacillus sp. AS-1 ATCC 55326 was redeposited as ATCC 69890 on Aug. 17, 1995 as AS-1A after elimination of cells which contaminated the original deposit ATCC 55326 over time. The characteristics of this strain are shown in Table 1.

TABLE 1

| | |
|---|---|
| 1. Morphology | Coccobacilli (oval, in pairs and short chains) |
| 2. Catalase | Negative |
| 3. Gram Reaction | Positive |
| 4. Type of Fermentation | Heterofermentative |
| 5. Gas from glucose (MRS broth) | Positive |
| 6. Type of lactic acid produced | DL-lactic |

TABLE 1-continued

| | |
|---|---|
| 7. Growth at 10° C. (in MRS broth) | Positive |
| 8. Growth at 30° C.[(1)] (in MRS broth) | Positive |
| 9. Growth at 37° C. (in MRS broth) | Positive |
| 10. Growth at 45° C. (in MRS broth) | Positive |
| 11. Growth at 50° C. (in MRS broth) | Negative |
| 12. Final pH in MRS broth with incubation at 30° C. for 24 hours | 4.4–4.6 |
| 13. Utilization of carbohydrates: | |
| glucose | Positive |
| galactose | Positive |
| fructose | Positive |
| lactose | Positive |
| xylose | Negative |
| rhamnose | Negative |

[(1)]Recommended temperature for activation and inhibition studies.

The culture is used at a level of about $10^6$ to $10^8$ cells per ml or gram of the food. The food is preferably refrigerated at between about 4° and 6° C.

Lactobacillus can be preserved for shipment by freezing, using various well known agents such as glycerol, sucrose and milk. The culture can also be lyophilized for shipment. Preferably the lyophilizing agent is milk.

SPECIFIC DESCRIPTION

EXAMPLE 1

Lactic acid producing bacteria were screened for their ability to inhibit other spoilage bacteria when the former are added to fresh raw milk which is held at 2°–5° C. FIG. 1 illustrates the ability of a Lactobacillus species (ATCC No. 55326) to inhibit *Pseudomonas aeruginosa* (ATCC No. 419). The photo shows the microbial condition of the milk after holding for 7 days in the presence of the Lactobacillus (left) or the absence (right). At 2°–5° C., raw milk inoculated with *P. aeruginosa* supports luxuriant growth of the organism while a duplicate sample of the same milk inoculated with 3% of an overnight culture ($10^7$ cells per ml or gram) of the Lactobacillus species failed to support such growth. The added *P. aeruginosa* (~100/ml) grew to $10^8$/ml in plain raw milk at 2°–5° C. while the Lactobacillus—supplemental milk maintained the same count for total Gram negative bacteria as the zero time control raw milk (~100/ml). Samples of the raw milk were plated by spreading on CVT agar, which is Standard Plate Count agar containing 1 ppm of 2, 3, 5-triphenyltetrazolium chloride and 50 ppm of crystal violet. This medium allows Gram negative bacteria to grow but inhibits gram positive types such as the added Lactobacillus sp. ATCC No. 55326.

EXAMPLE 2

In this example, the CFU/ml in raw milk for Lactobacillus AS-1 was $\leq 1.2 \times 10^7$. The raw milk was stored at 40°–41° F. for six days and then tested. Pseudomonas isolation agar and MacConkey agar (Difco, Detroit, Mich.) were used to enumerate Pseudomonas spp. and other Gram-negative bacteria including Salmonella spp., respectively.

The CFU/ml in the milk was $<4 \times 10^2$ at zero time for Pseudomonas or the other Gram-negative bacteria. Without any treatment, after 3 days of storage of the raw milk at 40° F., the CFU/ml was $10^4$, and after 6 days storage of the raw milk at 40° F., the CFU/ml was $10^6$.

With the addition of active culture of Lactobacillus ATCC No. 55326 ($\geq 10^7$/ml) to raw milk at zero time, the CFU/ml of group was $<10^2$ after storage for six days at 40° F. as shown in FIGS. 2 and 3.

EXAMPLE 3

*P. putida* was added to raw milk at four different levels and raw milk was stored at 40° F. for six days. Duplicate samples of the raw milk containing the four levels of *P. putida* were challenged with $\geq 10^7$ CFU/ml of Lactobacillus sp. ATCC No. 55326.

Four levels of *P. putida* used were:
(1) $1 \times 10^5$/ml
(2) $2.5 \times 10^3$/ml
(3) $<10^3$/ml
(4) $<10^2$/ml Lactobacillus sp. ATCC No. 55326 was used at a level of $10^7$ CFU/ml. Table 2 shows the results of the treatment with *P. putida* using the selective medium of Example 2 after cold storage (40°–41° F.) of raw milk for different day periods.

TABLE 2

| | 3-day | 5-day | 6-day |
|---|---|---|---|
| Level (1) alone | $>10^7$ | $>10^7$ | $>10^7$ |
| Level (1) + ATCC 55326 | $10^4$ | $10^4$ | $10^4$ |
| Level (2) alone | $>10^6$ | $>10^7$ | $>10^7$ |
| Level (2) + ATCC 55326 | $10^3$ | $10^3$ | $10^3$ |
| Level (3) alone | $>10^4$ | $>10^7$ | $>10^7$ |
| Level (3) + ATCC 55326 | $10^2$ | $10^2$ | $10^2$ |
| Level (4) alone | $>10^4$ | $>10^6$ | $>10^7$ |
| Level (4) + ATCC 55326 | $\leq 10^2$ | $\leq 10^2$ | $\leq 10^2$ |

As can be seen from Table 2, Lactobacillus sp. is very effective in inhibiting *P. putida*, *P. aeruginosa* and other spoilage bacteria in raw milk. It was found that the raw milk was not acidified by lactic acid production at low temperatures.

EXAMPLE 4

Table 3 shows the results of screening Lactobacillus sp. ATCC 55326 against various food-borne pathogens.

TABLE 3

| Pathogen | Inhibition (+) or No Inhibition (−) |
|---|---|
| 1. *Pseudomonas aeruginosa* | + |
| 2. *Escherichia coli* | + |
| 3. *Salmonella typhimurium* | + |
| 4. *Salmonella enteritidis* | + |
| 5. *Listeria monocytogenes* | − |
| 6. *Pseudomonas putida* ATCC 12633 | + |
| 7. *Pseudomonas nigrificance* | + |
| 8. *Escherichia coli* | + |

The method used was incubation of the milk containing the pathogens ($10^2$/ml) and also containing Lactobacillus sp. AS-1 (ATCC No. 55326) ($10^7$ CFU/ml) anion incubation at 4° C. for 7 days. Pathogens were enumerated by plating on appropriate selective medium.

The advantages of adding Lactobacillus sp. ATCC No. 55326 to raw milk during cold storage are as follows:

(1) Inhibition of Gram negative psychrotrophs, especially Pseudomonas spp. which grow at low temperature and decompose milk fat and proteins and thus affect milk quality. Decomposition of milk components by Pseudomonas spp. during cold storage stimulates the growth of health hazard pathogens such as *Listeria monocytogenes* as discussed by Marshall et al, Can. J. Microbiol. 37, 594–599 (1991).

(2) There is an antagonistic effect on food pathogens, especially Gram-negative bacteria present in low numbers such as Salmonella spp.

(3) There is an energy savings by using holding temperature of 40° F. rather than deep-cooling (36° F.) or thermization as is presently used in the art.

(4) Lactobacillus sp. ATCC No. 55326 added to raw milk at the specified level does not coagulate or significantly acidify raw milk stored at 40° F. for a week.

(5) Raw milk held for a week at 40° F. and containing $10^7$/ml Lactobacillus ATCC No. 55326 does not coagulate nor possess off-flavors when pasteurized. The same advantages are achieved in other foods, particularly dairy products.

The mechanism of inhibition by Lactobacillus sp. ATCC No. 55326 is believed to be by carbon dioxide production. In this regard, Roberts and Torrey (J. Dairy Sci. 71:52–60 (1988)) reported that refrigerated raw milk containing 20 to 30 millimolar $CO_2$ had significantly lower numbers of Pseudomonas and coliform bacteria than raw milk not treated to contain the $CO_2$. Also, filter sterilized culture supernatants of Lactobacillus species AS-1 (ATCC No. 55326) added to refrigerated (4° C.) raw milk and held for seven (7) days had no inhibitory effect on pathogenic or psychrotrophic bacteria which are inhibited by the viable Lactobacillus AS-1 cells. Such filter-sterilized supernatants also are not inhibitory for these bacteria when tested by the well or disk assay methods. It further was determined that the microorganism does not produce hydrogen peroxide; furthermore, inhibition of psychrotrophs and pathogens occur in the presence of catalase which degrades hydrogen peroxide and that it was not lactic acid production. It appeared that this strain produced an inhibitory effect, possibly by producing copious quantities of $CO_2$ more effectively competing for nutrients than the spoilage bacteria.

EXAMPLE 5

Lactobacillus AS-1 (Lactobacillus sp. ATCC No. 55326) was negative for hydrogen peroxide ($H_2O_2$) production. Two known $H_2O_2$ producers, ATCC *Lactobacillus lactis* strains 12315 and 39538, were used as positive controls and were in fact positive in the test. *Escherichia coli* was used as a negative control and it tested negative for $H_2O_2$ as expected.

Lactobacillus AS-1 was tested for its ability to produce hydrogen peroxide ($H_2O_2$) using the agar medium mentioned by Fontaine, E. A. et al., J. of Applied Bacteriology Vol. 69:326–331 (1990). The agar medium contained Rogosa agar to which was added a filter sterilized solution of peroxidase or catalase plus 2,2'.azino-bis (3-ethyl-benzthiazoline-6-sulphonic acid) (ABSA). For the filter sterilization, 20 mg of the catalase or peroxidase and 400 mg of the ABSA were dissolved in 100 ml of distilled water. Then 10 ml filter of the sterilized solution was added to 100 ml of the molten agar.

The two strains of *Lactobacillus lactis* (ATCC 12315 and 39538) were used as positive controls (producing $H_2O_2$) and the negative control was *E. coli* V517.

Lactobacillus AS-1 and the other two Lactobacilli were activated in MRS broth (100 ml) and *E. coli* was activated in BHI (Bovine Heart Infusion) for about 24 hours, except that Lactobacillus AS-1 was activated at 30° C. and the rest were at 37° C.

The prepared plates were inoculated using a loop and plates were incubated at 37° C. for 48 hours in a Gas Pak™ (anaerobic system).

No change in color of plates was noticed. However, when plates were further incubated at 37° C. aerobically (without a Gas Pak), purple colored colonies developed in about 2 hours at 37° C., aerobically in both strains of *Lactobacillus lactis* on plates containing peroxidase, but not on plates containing catalase.

After further incubation at 37° C. for ~24 hours aerobically the same results were obtained:

Lactobacillus AS-1 negative for $H_2O_2$

*Lactobacillus lactis* positive for $H_2O_2$ (both strains)

*E. coli* negative

In this test, colonies of bacteria producing $H_2O_2$ will form blue colonies aerobically but not anaerobically and only in the presence of peroxidase, not catalase. When no oxygen is present (anaerobic), $H_2O_2$ cannot be formed so incubating plates anaerobically gave negative results as expected. When the plates were further incubated aerobically, purple colonies formed as the $H_2O_2$ formed then oxidized the indicator dye 2,2.azino-bis (3-ethyl-benzthiazoline-6-sulphonic acid) (ABSA) to a purple color. Lactobacillus AS-1 was negative for $H_2O_2$ production while the two positive controls were positive and the negative control was negative.

EXAMPLE 6

Another experiment proved that Lactobacillus AS-1 does not produce $H_2O_2$. This experiment concerned the effect of the enzyme catalase, which converts $H_2O_2$ to hydrogen and oxygen, on the inhibitory activity of Lactobacillus AS-1. The rationale was that if catalase destroyed the inhibitory activity of Lactobacillus AS-1, then the ability to inhibit other bacteria (*Escherichia coli* in this case) would be destroyed if it produced $H_2O_2$. The catalase did not prevent the ability of Lactobacillus AS-1 from inhibiting the growth of *E. coli*, which was 600 CFU/ml at zero time and less than 100 CFU/ml in the raw milk after incubating at 40° F. (4° C.) for six days.

Fresh raw milk was inoculated with approximately $6 \times 10^2$ CFU/ml of active *E. coli* V517 (activated in BHI @ 37° C. for ~24 hours).

Also, the milk was inoculated with 3% by volume of an activated broth (MRS) culture of Lactobacillus AS-1.

Catalase was added to raw milk at 0.01% concentration. This solution was filter sterilized before addition. Autoclaved catalase (121° C. for 15 minutes) was added as a control.

Raw milk was incubated at 40° F. (~4° C.) for six days.

The number of *E. coli* V517 was evaluated using both MacConkey agar (Difco, pages 546–550, 10th Edition) and EMB agar (Difco, pages 324–326, 10th Edition) by spreading 0.1 ml of 1/10 dilution of raw milk).

Plates were incubated @ 37° C. for 48 hours.

Count of *E. coli* V517 was less than $10^2$ in both catalase and non-catalase treated samples. PH of raw milk was ~6.0 after six days vs. 6.6 of raw milk not inoculated with Lactobacillus AS-1.

The data shows that Lactobacillus AS-1 does not produce $H_2O_2$ and therefore its ability to inhibit bacteria in pasteurized or raw milk under refrigeration is due to an effect other than producing $H_2O_2$.

EXAMPLE 7

Tests were performed to confirm that Lactobacillus sp. (ATCC 69890; AS-1A) was inhibitory against Gram negative psychrotrophs in milk, and to compare the inhibition of two Lactobacillus strains obtained from *Lactobacillus casei* subspecies NRRL-B-12344 of U.S. Pat. No. 4,912,047 to Matrozza et al and Lactobacillus sp. 18261 of U.S. Pat. No. 4,874,704 to Boudreaux et al.

Sterile skim milk was inoculated with *Pseudomonas putida*, obtained from milk and a known representative Gram negative psychrotroph of milk, and was divided into five 100 ml portions. Overnight cultures of tested strains were added to each portion of milk at about $10^7$ CFU/ml. The inoculated milk was stored at 4° C. and samples were withdrawn for a plate count at 1, 2 and 3 weeks. The results are means of duplicate plates.

Table 1 shows the comparison of inhibition against the *Pseudomonas putida* in milk by the Lactobacillus sp. ATCC 69890 (AS-1A).

TABLE 1

| | *P. putida* CFU/ml | | | |
|---|---|---|---|---|
| Treatment* | Day-0 | Day-7 | Day-14 | Day-21 |
| Control | 350 | $1.2 \times 10^6$ | $6.2 \times 10^7$ | $1.2 \times 10^8$ |
| AS-1A | 350 | 310 | 300 | 100 |
| B-12346 | 350 | $7.3 \times 10^4$ | $1.3 \times 10^5$ | $1.3 \times 10^7$ |
| B-18261 | 350 | $2.1 \times 10^5$ | $3.6 \times 10^6$ | $5.9 \times 10^7$ |

*About $2 \times 10^7$ CFU/ml cells in MRS medium overnight culture were added to each treatment at 0 time;

Lactobacillus sp. AS-1A shows significant inhibition to Gram negative psychrotroph *P. putida* in skim milk at 4° C. Growth of inoculated *P. putida* was completely inhibited for three weeks in milk containing $2 \times 10^7$ CFU/ml AS-1A cells. The other Lactobacillus species (NRRL-B-12344 and NRRL-B-18261) show virtually no inhibition by comparison under the same testing conditions. Thus, Lactobacillus sp. AS-1A is a unique strain which provides inhibition of psychrotrophic bacteria in milk products.

It is intended that the foregoing specification be only illustrative of the present invention and that the present invention be limited to the hereinafter appended claims.

We claim:
1. A biologically pure culture of Lactobacillus sp. ATCC No. 69890.
2. A composition consisting essentially of the culture of claim 1 and a suitable carrier which is frozen for storage and shipment.
3. A composition consisting essentially of the culture of claim 1 and a suitable carrier which is lyophilized for storage and shipment.
4. A composition of the culture of claim 1 and a suitable carrier where there are between about $10^6$ and $10^{12}$ cells per gram of the culture.

* * * * *

UNITED STATES PATENT AND TRADEMARK OFFICE
CERTIFICATE OF CORRECTION

Figure 1B:
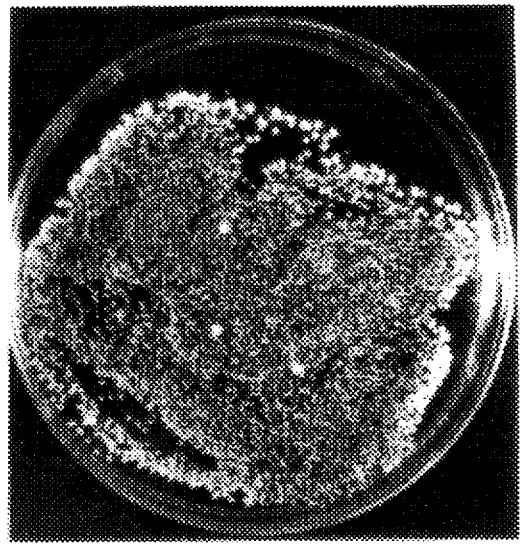

PATENT NO. : 5,759,843          Page 1 of 2
DATED      : June 2, 1998
INVENTOR(S): William E. Sandine and Nageb S. Al-Zoreky It is certified that error appears in the above-identified patent and that said Letters Patent is hereby corrected as shown below:

Column 2, line 1, "Fig. 1 is a photograph" should be --Figures 1A and 1B are photographs--.

Figure 2A:
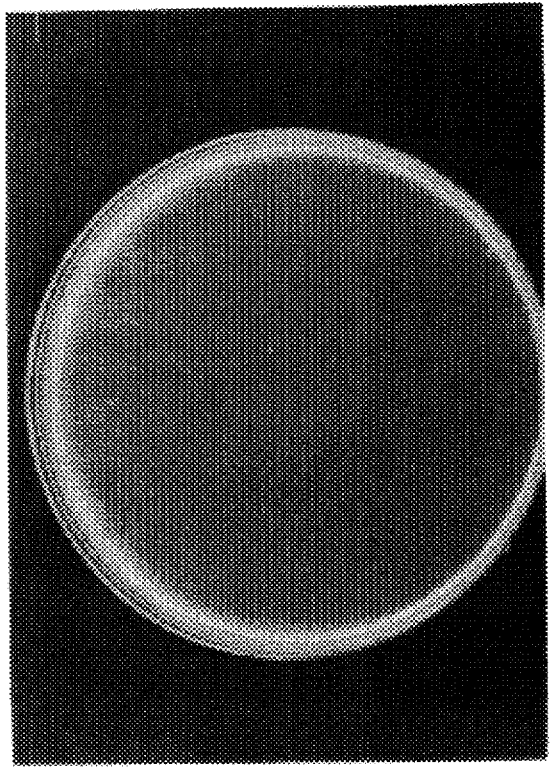
FIG. 2 is a photograph showing spiral plate enumeration of bacteria present in 50 ml of raw milk held 6 days at 40° F. in the presence of $10^7$ CFU/ml of Lactobacillus sp. As-1 (ATCC No. 55326) (left) or absence of ATCC No. 55326 (right) after incubation of plates of Pseudomonas isolation agar 48 hours at 30° C.
Figure 2B:
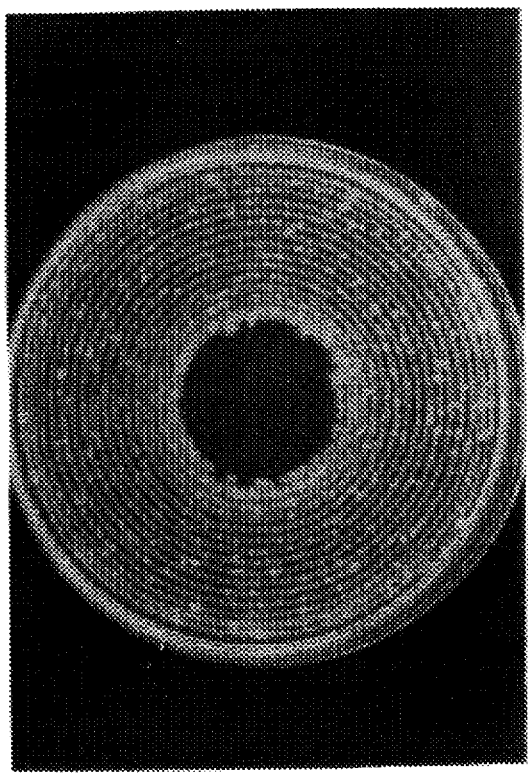
Figure 2A:
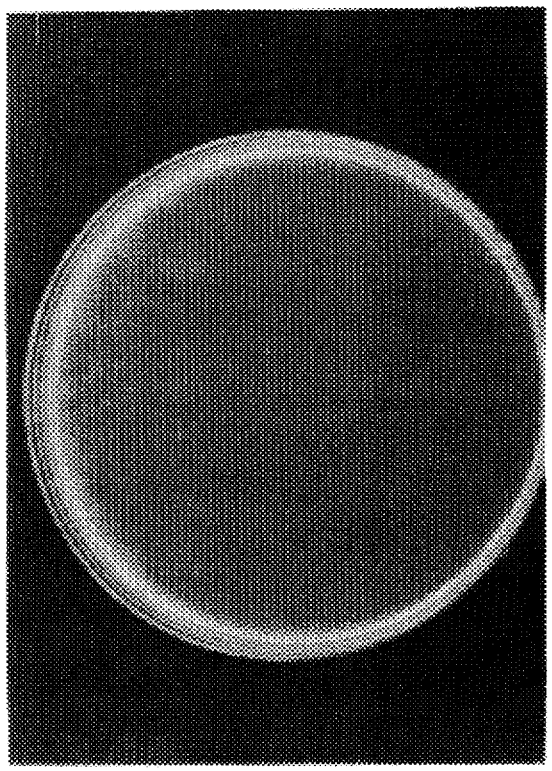
Figure 2B:
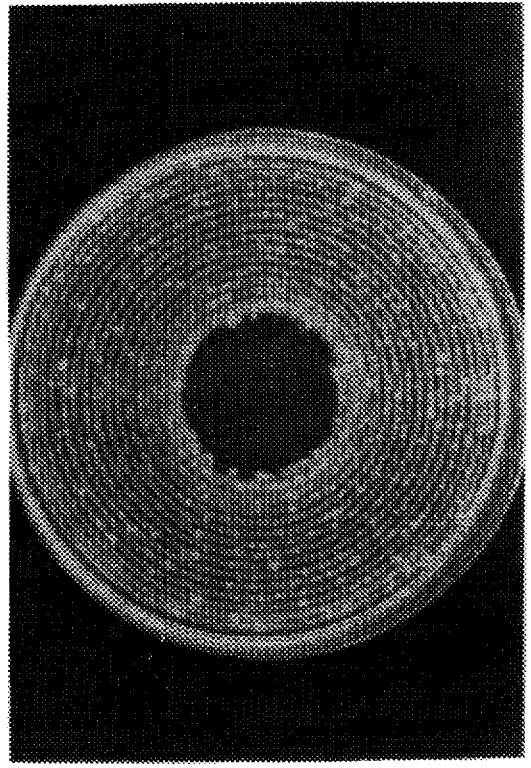

Column 2, line 10, "Fig. 2 is a photograph", should be --Figures 2A and 2B are photographs--.

Figure 3A:
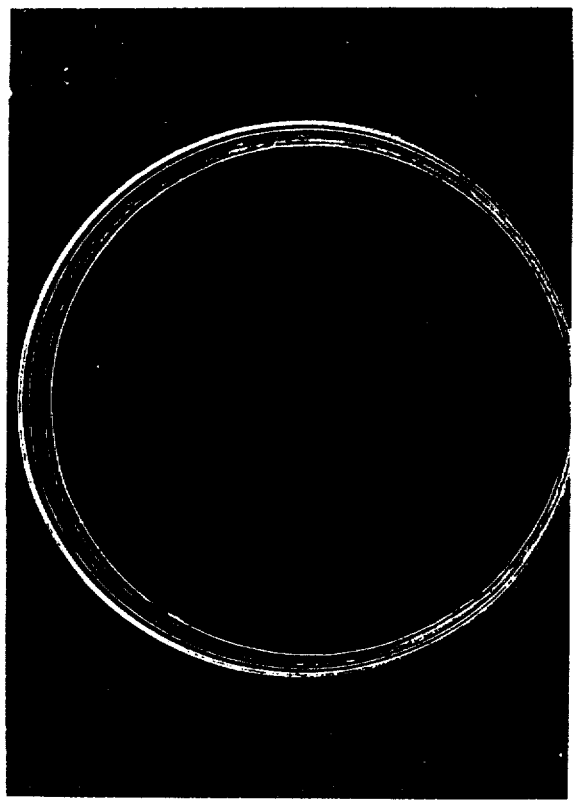
FIG. 3 is a photograph showing spiral plate enumeration of bacteria present in 50 ml of raw milk held 6 days at 40° F. in the presence of $10^7$ CFU/ml of Lactobacillus sp. AS-1 (ATCC No. 55326) (left) or absence of ATCC No. 55326) (right) after incubation of plates of MacConkey agar at 37° C. for 48 hours.
Figure 3B:

Column 2, line 15, "Fig. 3 is a photograph", should be --Figures 3A and 3B are photographs--.

Column 3, line 32, "FIG. 1 illustrates", should be --Figures 1A and 1B illustrate--.

Column 4, line 2, "FIGS. 2 and 3" should be --Figures 2A, 2B, 3A and 3B--.

Figures 3A and 3B should be added as per attached.

Signed and Sealed this

Tenth Day of November 1998

Attest:

BRUCE LEHMAN

Attesting Officer          Commissioner of Patents and Trademarks